(12) United States Patent
Dakin

(10) Patent No.: US 10,188,111 B2
(45) Date of Patent: Jan. 29, 2019

(54) PHARMACEUTICALLY ACCEPTABLE COMPOSITION COMPRISING DILUTE SODIUM HYPOCHLORITE SOLUTION

(71) Applicant: Hypo-Stream Limited, Melbourne (GB)

(72) Inventor: Myles H. E. Dakin, Cambourne (GB)

(73) Assignee: Hypo-Stream Limited, Melbourne (GB)

( * ) Notice: Subject to any disclaimer, the term of this patent is extended or adjusted under 35 U.S.C. 154(b) by 229 days.

(21) Appl. No.: 15/286,504

(22) Filed: Oct. 5, 2016

(65) Prior Publication Data

US 2017/0020135 A1    Jan. 26, 2017

Related U.S. Application Data

(62) Division of application No. 13/639,224, filed as application No. PCT/GB2011/050729 on Apr. 13, 2011.

(30) Foreign Application Priority Data

Apr. 14, 2010 (GB) .................................... 1006187
Feb. 8, 2011 (GB) .................................... 1102135

(51) Int. Cl.
| | |
|---|---|
| A01N 59/08 | (2006.01) |
| A61L 2/22 | (2006.01) |
| A61J 1/10 | (2006.01) |
| A61J 1/18 | (2006.01) |
| A61J 1/20 | (2006.01) |
| A61J 7/00 | (2006.01) |
| A61M 5/142 | (2006.01) |
| A61M 5/19 | (2006.01) |
| A61M 35/00 | (2006.01) |
| A61M 11/00 | (2006.01) |

(52) U.S. Cl.
CPC ................ *A01N 59/08* (2013.01); *A61J 1/10* (2013.01); *A61J 1/18* (2013.01); *A61J 1/2093* (2013.01); *A61J 7/0046* (2013.01); *A61L 2/22* (2013.01); *A61M 5/14248* (2013.01); *A61M 5/19* (2013.01); *A61M 11/007* (2014.02); *A61M 35/003* (2013.01); *A61M 35/00* (2013.01)

(58) Field of Classification Search
None
See application file for complete search history.

(56) References Cited

U.S. PATENT DOCUMENTS

| | | | |
|---|---|---|---|
| 1,522,601 A | 1/1925 | Strobel | |
| 1,859,316 A | 5/1932 | Sponsel | |
| 3,918,612 A | 11/1975 | Voulgaris | |
| 4,850,729 A | 7/1989 | Kramer et al. | |
| 5,171,219 A | 12/1992 | Fujioka et al. | |
| 5,391,351 A | 2/1995 | Kaufman | |
| 5,489,280 A | 2/1996 | Russell | |
| 5,855,922 A | 1/1999 | Danner et al. | |
| 7,393,522 B2 | 7/2008 | Najafi et al. | |
| 9,072,726 B2 | 7/2015 | Alimi et al. | |
| 2002/0114851 A1 | 8/2002 | Camper et al. | |
| 2004/0232381 A1 | 11/2004 | Pinza et al. | |
| 2004/0256330 A1 | 12/2004 | Okazaki | |
| 2007/0232694 A1* | 10/2007 | Phillips .................. | A01N 59/00 514/518 |
| 2008/0267812 A1 | 10/2008 | Kawachi et al. | |
| 2010/0112680 A1 | 5/2010 | Brockwell et al. | |
| 2010/0218790 A1 | 9/2010 | Reis et al. | |
| 2010/0284951 A1 | 11/2010 | Pongprapansiri et al. | |

FOREIGN PATENT DOCUMENTS

| | | |
|---|---|---|
| CH | 690311 A5 | 7/2000 |
| CN | 1596989 A | 3/2005 |
| CN | 201248920 Y | 6/2009 |
| FR | 2593704 A1 | 8/1987 |
| GB | 1418193 A | 12/1975 |
| JP | 60-031818 A | 2/1985 |
| JP | 61-056064 A | 3/1986 |
| JP | 09-066100 A | 3/1997 |
| JP | 11-188083 A | 7/1999 |
| JP | 11-255502 A | 9/1999 |
| JP | 11-302886 A | 11/1999 |
| JP | 2007517064 A | 6/2007 |
| JP | 2008534516 A | 8/2008 |
| JP | 2010-022663 A | 2/2010 |
| KR | 10-0836570 | 6/2008 |
| RU | 2229864 C1 | 6/2004 |
| RU | 2320329 C1 | 3/2008 |
| WO | WO-90/05529 A1 | 5/1990 |
| WO | WO-2004/098657 A1 | 11/2004 |
| WO | WO-2005/054138 A1 | 6/2005 |

(Continued)

OTHER PUBLICATIONS

"Dakin's Solutions Full Strength", Century Pharmaceuticals, downloaded from the Internet at: <http://dakins.net/full-strength/> (product developed 1914).

Danilkov et al., [Effects of indirect electrochemical blood oxidation by sodium hypochlorite solution on the course on inflammatory process in the kidneys and urinary tract], [Article in Russian], Urol. Nefrol. (Mosk), (3):25-7 (May 1998), Abstract Only.

El Kebir et al., Role of neutrophil apoptosis in the resolution of inflammation, ScientificWorldJournal, 10:1731-48 (2010).

(Continued)

*Primary Examiner* — Susan T Tran

(74) *Attorney, Agent, or Firm* — Marshall, Gerstein & Borun LLP

(57) ABSTRACT

A pharmaceutically acceptable composition comprising dilute stabilized sodium hypochlorite solution and an indicator to show that the dilute stabilized sodium hypochlorite solution is fresh and active.

36 Claims, 9 Drawing Sheets

(56) References Cited

FOREIGN PATENT DOCUMENTS

| WO | WO-2006/131747 A1 | 12/2006 |
| WO | WO-2007/070861 A1 | 6/2007 |
| WO | WO-2009/023503 A1 | 2/2009 |
| WO | WO-2009/046692 A2 | 4/2009 |
| WO | WO-2010/006442 A1 | 1/2010 |
| WO | WO-2010/148004 A1 | 12/2010 |
| WO | WO-2011/128682 A2 | 10/2011 |
| WO | WO-2012/123695 A2 | 9/2012 |

OTHER PUBLICATIONS

Lindfors, A Comparison of an Antimicrobial Wound Cleanser to Normal Saline in Reduction of Bioburden and its Effect on Wound Healing, Ostomy Wound Manage., 50(8):28-41 (2004).
Vincent et al., "Evaluation of an Antitumor Cell Wound Irrigant—Milton, a Stable Hypochlorite," *Cancer*, 17:997-1005 (1964).
International Search Report and Written Opinion for Application No. PCT/GB2011/050729, dated Dec. 2, 2011.
International Preliminary Report on Patentability for Application No. PCT/GB2011/050729, dated Oct. 16, 2012.

\* cited by examiner

PHARMACEUTICALLY ACCEPTABLE COMPOSITION COMPRISING DILUTE SODIUM HYPOCHLORITE SOLUTION

CROSS-REFERENCE TO RELATED APPLICATION

This application is a divisional of U.S. patent application Ser. No. 13/639,224, filed Dec. 6, 2012, which is the National Stage of PCT/GB/2011/050729, filed Apr. 13, 2011, and which claims priority to Great Britain Application No. 1102135.9, filed Feb. 8, 2011, and Great Britain Application No. 1006187.7, filed Apr. 14, 2010, all of which are expressly incorporated herein by reference and made a part hereof.

The invention relates to a dilute disinfectant solution, for example, a dilute solution of stabilized sodium hypochlorite solution.

BACKGROUND TO THE INVENTION

The use of a dilute solution of Milton®, a stabilized electrolytically prepared solution of 1.13% sodium hypochlorite, as a wound irrigant is described in "Evaluation of an antitumor cell wound irrigant—Milton, a stable hypochlorite" published in 1964 by the Wellcome Laboratories for Medicine and Surgery. As discussed in this article, it is essential for a wound irrigant to be non-toxic and safe to use. Various dilutions are disclosed in the article and the operative safety of these dilutions is shown.

The present applicant has recognized that such dilute disinfectant solutions degrade over time and thus need to be mixed when required. Furthermore, the present applicant has recognized that said solutions need to be recognized as fresh via use of an indicator and they need to be delivered to the site of need via a sterile delivery device that is simple to use, especially in clinical applications including within medicine, dentistry and veterinary surgery.

STATEMENT OF THE INVENTION

According to a first aspect of the invention there is provided a portable device for mixing a dilute disinfectant solution comprising a disinfectant reservoir holding said disinfectant solution, a chamber which is connected to said disinfectant reservoir and which is for holding a predetermined amount of dilutant, disinfectant discharging means for discharging a predetermined amount of said disinfectant solution from said first reservoir to be mixed with said predetermined amount of dilutant, whereby said device provides the dilute disinfectant solution at a fixed dilution determined by the ratio of the predetermined amount of said disinfectant solution to the predetermined amount of dilutant.

In this way, the dilute disinfectant solution can be mixed when needed. As explained in more detail below, the mixing is simple and quick for the user but still done in a clinically acceptable manner. The proposed devices are preferably cheap to manufacture and in some embodiments sterilizable and disposable to prevent contamination.

The device may further comprise an indicator (or second) reservoir for an indicator indicating the activity of the dilute disinfectant solution. The indicator reservoir may be a separate reservoir and the device may further comprise indicator discharging means for discharging a predetermined amount of said indicator from said second reservoir to be mixed with said predetermined amount of dilutant and said predetermined amount of disinfectant. Alternatively, the indicator reservoir may be integral with either the disinfectant reservoir or the dilutant reservoir. In other words, the indicator may be pre-mixed with the disinfectant in the disinfectant reservoir or pre-mixed with the dilutant in the dilutant reservoir. Furthermore, the indicator may be formed from the combination of components contained partly in the dilutant reservoir and partly in the disinfectant reservoir. In this case, the disinfectant and/or dilutant discharging means provide the indicator discharging means.

Thus according to another aspect of the invention there is provided a disinfectant composition comprising dilute stabilized sodium hypochlorite solution and an indicator to show that the dilute sodium hypochlorite solution is fresh and active.

According to another aspect of the invention there is provided a pharmaceutically acceptable composition comprising dilute stabilized sodium hypochlorite solution and an indicator to show that the dilute sodium hypochlorite solution is fresh and active. The pharmaceutically acceptable composition may further comprise a pharmaceutically acceptable dilutant or carrier. The pharmaceutically acceptable composition may be used in medicine, in particular for preventing infection and aiding healing. Another aspect of the invention provides use of dilute disinfectant solution in the manufacture of the pharmaceutically acceptable composition for use in preventing infection. According to another aspect of the invention, there is provided a method of treating infection in a mammal comprising administering an effective amount of the composition defined above to said mammal.

According to another aspect of the invention, there is provided a method of assessing the disinfecting activity of dilute stabilized sodium hypochlorite solution, the method comprising mixing said solution with an indicator to show that the dilute stabilized sodium hypochlorite solution is fresh and active.

The predetermined amount of dilutant and the predetermined amount of disinfectant solution are determined so as to provide the desired dilution of the stabilized disinfectant solution. The dilutant may be water.

The disinfectant solution in the first reservoir may be a stabilized sodium hypochlorite solution at 1% or 2% sodium hypochlorite, e.g. a disinfectant known as "Milton's Solution" comprising sodium chloride. The dilute disinfectant solution may be a 2.5%-10% solution of Milton's solution diluted in water where the disinfectant solution is 2% sodium hypochlorite. The sodium chloride in said solution is typically at a concentration of 16.5%. Thus, the ratio of predetermined amount of disinfectant solution to predetermined amount of water may be in the range between 1 to 10 to 1 to 40. Alternatively, the dilute disinfectant solution may be a 5% to 20% solution of Milton's solution diluted in water where the disinfectant solution is 1% sodium hypochlorite. In this case, ratio of the predetermined amount of disinfectant solution to predetermined amount of water to may be in the range between 1 to 5 to 1 to 20.

In both cases, the predetermined amount of water and the predetermined amount of disinfectant solution may be such that the dilute disinfectant solution may be a buffered sodium hypochlorite solution where the sodium hypochlorite is in a concentration range of 0.025%-0.2%, preferably 0.05%-0.1%. The buffering of the sodium hypochlorite solution can provide stabilization of the dilute disinfectant solution.

The dilute disinfectant solution may be used as a disinfectant solution for use as an irrigating solution for surgical sites or wounds. The solution can also be used for a mouth rinse after oral surgery, dental surgery or following oral hygiene procedures. Thus according to another aspect of the invention, there is provided a portable device for mixing a dilute disinfectant solution to be used as a mouth rinse comprising a first reservoir for said disinfectant solution, a second reservoir for an indicator indicating the activity of the dilute disinfectant solution, a chamber which comprises indication means to indicate to a user the amount of water to be added to the chamber and which is connected to said first and second reservoirs, means for discharging a predetermined amount of said disinfectant solution from said first reservoir into said chamber and means for discharging a predetermined amount of said indicator from said second reservoir into said chamber, wherein said predetermined amounts of said disinfectant solution and said indicator are mixed with a predetermined amount of water in said chamber to provide the dilute disinfectant solution.

The indicator indicates the activity of the dilute disinfectant solution, in other words, the indicator shows the dilute disinfectant solution is fresh and active. The indicator is not the active ingredient of the dilute disinfectant solution. The indicator preferably degrades over time when mixed with the dilute disinfectant solution. In other words, the indicator preferably does not degrade over time when mixed with either neat dilutant or neat disinfectant. In this way, the indicator may be included in either the dilutant or disinfectant reservoir rather than in a separate reservoir. The indicator may comprise a first component which shows the dilute disinfectant solution is fresh and active and a second component which degrades the first component. In this case, the first and second components may be incorporated one in the dilutant reservoir and one in the disinfectant reservoir. Alternatively, two additional reservoirs may be included.

The indicator (e.g. first component) may be a dye or a flavor or combination thereof (e.g. in a mouthwash). The indicator preferably produces a noticeable change over time to a user of the dilute disinfectant solution. For example, for a dye, there is either a significant color change or the solution becomes colorless. For a flavor, there is a noticeable degradation of the flavoring such that the solution becomes unpalatable. Since the resultant solution is most effective, if diluted immediately prior to use, the noticeable change may occur within a time frame of 45 minutes to 1 hour. In this time frame, the noticeable change occurs prior to the loss of therapeutic action of dilute disinfectant solution.

The dye may be a dye such as those which are routinely used in surgical procedures with no adverse effects. Examples of suitable dyes include azafloxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red. The predetermined amount of dye is preferably low enough to prevent interaction with active components but great enough so that the dye color is visible within the dilute disinfectant solution.

The indicator may be organic or inorganic, biocompatible, non-toxic and pharamaceutically acceptable.

In one aspect of the invention, the indicator (preferably a dye) may indicate the strength or dilution of the disinfectant. For example, if the disinfectant is diluted by ten (1 part disinfectant in 10 parts of water) then the indicator dye would be blue. If the dilution is diluted by 20 (1 part of disinfectant in 20 parts of water) the indicator would be green. If the disinfectant is diluted by 30 (1 part disinfectant in 30 parts of water) then the indicator dye would be orange. If the disinfectant is diluted by 40 (1 part disinfectant in 40 of water) then the indicator dye would be red. In such an aspect, the indicator dye may preferably be packaged with the specific dilution.

In another aspect of the present invention, the indicator may also show that the disinfectant is at the correct dilution.

In yet another aspect of the present invention, the indicator may be an organic or inorganic dye which can be degraded by the chemical action of the disinfectant, e.g. the innate oxidative capacity of the hypochlorite disinfectant.

The indicator may suffer a diminishment of intensity over a period of 1 hour. This indicates the activity of the disinfectant is not sufficiently reliable to produce the clinical action desired.

In another preferred embodiment, the indicator is selected so that it degrades and shows a change in property over the same period in which the activity of the chosen dilution of said disinfectant degrades. For example, one dye might change from colored to colorless over 30 minutes, while another might make this change over 1 hour while another might take 2 hours. This might be useful for different dilutions of disinfectant where the concentration is critical, e.g. in surgical situations such as the disinfecting of dirty wounds, gunshot wounds or a slower trickle irrigation of a surgical site that is uncontaminated.

Where the indicator is a dye, the color degradation of the indicator dye may be used as an indicator of the reduction in activity of the disinfectant. The intensity of the color can be measured by comparison to a set color charts or with a calibrated optical measuring device to indicate disinfectant activity.

The dilute disinfectant can have an indicator such as a dye added after its dilution to indicate continued activity. For example, the dilute disinfectant (e.g. Milton's number 2 solution diluted with water) may have an indicator dye added to it for the first time after the dilution or additional indicator dye may be added to indicate continued activity.

In one embodiment of the invention, the indicator may be an indicator dye which is an unstable compound which spontaneously degrades over a period of time (preferably from 30 minutes to 2 hours, e.g. over 30 minutes, 45 minutes, 1 hour or 2 hours). In this embodiment, the indicator is preferably formed at the time of dilution of the disinfectant by adding two separate components together in order to generate the indicator dye. Once generated it is then added to the dilute disinfectant solution, after which the indicator dye "degrades" from exhibiting color (e.g. red, blue or green) to being colorless.

The dilutant, disinfectant and indicator may be simultaneously mixed or the dilutant and disinfectant mixed first with the indicator discharging means arranged to discharge the indicator into the dilute disinfectant.

In one embodiment of the invention, the volume of dilute disinfectant solution provided by the device may be 1 liter. The predetermined amount of dilutant may be 945 ml of water and the predetermined amount of disinfectant may be 50 ml of Milton 2% (i.e. 2% hypochlorite in 16.5% sodium chloride). The predetermined amount of indicator may be 5 ml of methylene blue. Thus the dilute disinfectant solution has 94.5% dilutant, 5% disinfectant and 0.5% indicator. In this case, the freshly mixed solution is blue. After 30 minutes, the solution is blue with diminished hue and after 1 hour the color is virtually absent.

In an alternative embodiment of the invention, the volume of dilute disinfectant solution provided by the device may be 1 liter. The predetermined amount of dilutant may be 880 ml of water and the predetermined amount of disinfectant may be 100 ml of Milton 2% (i.e. 2% hypochlorite in 16.5% sodium chloride). The predetermined amount of indicator may be 20 ml of methylene green. Thus the dilute disinfectant solution has 88% dilutant, 10% disinfectant and 2% indicator. In this case, the freshly mixed solution is green. After 30 minutes, the solution is green with diminished hue and after 1 hour the color is virtually absent.

In an alternative embodiment of the invention, the volume of dilute disinfectant solution provided by the device may be 1 liter. The predetermined amount of dilutant may be 970 ml of water and the predetermined amount of disinfectant may be 25 ml of Milton 2% (i.e. 2% hypochlorite in 16.5% sodium chloride). The predetermined amount of indicator may be 5 ml of gentian violet. Thus the dilute disinfectant solution has 97% dilutant, 2.5% disinfectant and 0.5% indicator. In this case, the freshly mixed solution is violet. After 30 minutes, the solution is violet with diminished hue and after 1 hour the color is virtually absent.

In each embodiment, the diminishing hue (e.g. blue, green or violet) indicates that the dye is being degraded at a rate that approximates the gradual reduction in concentration of the active hypochlorite. After 1 hour, there may be active hypochlorite present but it is not verifiably adequate to guarantee full clinical efficacy. The indicator thus acts as a safeguard to ensure the solution is used within a time period where the therapeutic concentration is maintained and that it is also withheld once the color intensity indicates inadequate levels of active hypochlorite. It will be appreciated that several alternative combinations of indicator dyes and dilutant may be used and the examples given above are not exhaustive nor restrictive.

In one particularly preferred embodiment of the invention, the dilute disinfectant solution is a buffered dilute sodium hypochlorite solution, wherein said dilute stabilized sodium hypochlorite solution is buffered to a pH of from 5-10, preferably 6-8. The buffer may be any buffer suitable to maintain the pH of the dilute solution at the desired pH and, if the solution is to be used pharmacologically, then it must be pharmaceutically acceptable. Typical examples of suitable buffers for use include buffers selected from the group consisting of a phosphate/phosphoric acid buffer, a borate/boric acid buffer, a citrate/citric acid buffer and a citrate/citric acid buffer.

Dilute sodium hypochlorite solutions such as dilute Milton's solutions 1 and 2 typically also include a stabilizer such as sodium chloride.

The disinfectant reservoir is preferably opaque to prevent degradation of the disinfectant solution due to light exposure.

Thus according to another aspect of the invention, there is provided a device for mixing a dilute disinfectant solution comprising a first reservoir for said disinfectant solution, a chamber connected to said first reservoir and means for discharging a predetermined amount of said disinfectant solution from said first reservoir into said chamber, wherein said predetermined amount of said disinfectant solution is mixed with a predetermined amount of dilutant in said chamber to provide the dilute disinfectant solution and wherein said first reservoir is configured to prevent the disinfectant solution therein being exposed to light.

The first reservoir may have opaque walls. The predetermined amounts of disinfectant solution and dilutant may be as described above. A second reservoir of indicator may be added to the device as described above. The aspects of the invention may thus be combined.

The device may be arranged to prevent dispensing neat disinfectant. Dispensing neat disinfectant may be dangerous because of the acute short term irritation and also long term because undiluted disinfectant does not degrade. For example, the device may comprise an outlet for the dilute disinfectant and there may be no direct access from the disinfectant reservoir to the outlet. Thus the indicator discharging means and/or the disinfectant discharging means may be arranged to discharge said indicator and/or said disinfectant into said chamber. The dilute disinfectant may then be provided from the chamber which is connected to the outlet.

The device may also be arranged to prevent dispensing neat dilutant. This is dangerous in the sense that the clinician is using dilutant rather than dilute disinfectant solution and thus not obtaining the clinical benefit.

The device may be provided with a mechanism (e.g. locking mechanism) which prevents the device providing a discharge, e.g. a discharge of neat disinfectant and/or a discharge of neat dilutant. The locking mechanism preferably prevents discharging from an outlet of the device before mixing the dilute disinfectant. The locking mechanism may be in the form of a friable seal which may only be broken after mixing.

The disinfectant reservoir may hold only said predetermined amount of said disinfectant solution. In this case, said disinfectant discharging means is preferably arranged to wholly and completely discharge said predetermined amount of said disinfectant solution from said disinfectant reservoir. Similarly, the indicator reservoir may hold only said predetermined amount of said indicator and/or said indicator discharging means may be arranged to wholly and completely discharge said predetermined amount of said indicator from said indicator reservoir.

The chamber may be a dilutant reservoir holding only said predetermined amount of dilutant. Thus according to another aspect of the invention, there is provided portable device for mixing a dilute disinfectant solution comprising a first reservoir comprising a predetermined amount of said disinfectant solution, a chamber which is connected to said first reservoir and which holds a predetermined amount of dilutant, and means for discharging said predetermined amount of said disinfectant solution from said first reservoir into said chamber to be mixed with said predetermined amount of dilutant in said chamber wherein said device provides the dilute disinfectant solution at a fixed dilution determined by the ratio of the predetermined amount of said disinfectant solution to the predetermined amount of dilutant. The predetermined amount of said disinfectant is preferably wholly and completely discharged into the predetermined amount of dilutant. Since the dilutant and disinfectant reservoirs hold only the predetermined amounts of dilutant and disinfectant, once they are mixed, the device has been used. In other words, the device may only be used once, then it is discarded. The device is thus a single use or one-off use device.

Alternatively, the device may further comprise dilutant discharging means for discharging said predetermined amount of dilutant, the dilutant discharging means being arranged to simultaneously discharge said predetermined amount of dilutant from said chamber as said disinfectant discharging means discharges said predetermined amount of disinfectant whereby said disinfectant solution is mixed with said dilutant as the device provides the dilute disinfectant solution. In other words, the liquids are simultaneously dispensed with mixing occurring at the point of dispensing. In one embodiment, the dilutant reservoir may hold only the predetermined amount of dilutant and the disinfectant reservoir may hold only the predetermined amount of disinfectant and both predetermined amounts may be discharged wholly and completely on activation. Thus, in this way, the device may only be used once, then it is discarded.

Alternatively, the device may further comprise a dilutant reservoir for dilutant which is connected to the chamber and dilutant discharging means for discharging said predetermined amount of dilutant from said dilutant reservoir into said chamber. The dilutant reservoir may be connected to the chamber via an additional dilutant reservoir which holds the predetermined amount of dilutant. Similarly, the disinfectant reservoir may be connected to the chamber via an additional disinfectant reservoir which holds the predetermined amount of disinfectant. Either or both of the additional disinfectant reservoir and additional dilutant reservoir may be integral with the chamber. In these arrangements, more than one dose of diluted disinfectant may be dispensed from the device.

In this case, the dilutant and/or disinfectant discharging means may be in the form of a pumping mechanism which draws dilutant and/or disinfectant from the main reservoirs into the additional reservoirs. The pumping mechanism may comprise a single pump which draws dilutant and disinfectant from the main reservoirs into the additional reservoirs during a singe stroke. In this case, the portions of the single stroke during which the additional reservoirs draw from the main reservoirs determines the mixing ratio. As an alternative, the pumping mechanism may comprise two or more pumps arranged to work synchronously, each one drawing fluid from each reservoir simultaneously. The drawn fluid passes into a common outlet or a set of closely spaced outlets. In this case, the ratio of the pumping volume per stroke sets the desired mixing ratio of the two fluids. The pump(s) may be positive displacement plunger pumps.

Alternatively, the chamber is a dilutant reservoir comprises indication means to indicate to a user the amount of dilutant to be added to the reservoir, e.g. the chamber is in the form of a cup and the device delivers dilute disinfectant solution is to be used as a mouth rinse.

The means for discharging the predetermined amounts of disinfectant solution, dilutant and/or indicator may be a pump. The pump may be manually controlled, e.g. by depression of a button. Alternatively, the means may be in the form of a syringe or similar device which is manually discharged into the chamber. Alternatively, the means may be in the form of a twist or push activation mechanism. The means may be a friable membrane which is ruptured by a user (e.g. following activation of the twist or push mechanism) to discharge said predetermined amount of said disinfectant solution. The device may be configured such that opening of the device initiates the discharging of any one or all of the predetermined amounts of disinfectant solution, dilutant and/or indicator.

The device may be in the form of a drip bag. In this case, the main body of the drip bag may be the dilutant reservoir which may hold dilutant in the range 250 ml to 2 liters. The disinfectant reservoir and the indicator reservoir (where used) may be mounted externally or internally to the dilutant reservoir. The disinfectant discharging means and the indicator discharging means (where used) may be arranged to wholly and completely discharge the disinfectant and indicator (where used) into the dilutant reservoir. The disinfectant discharging means and the indicator discharging means may be in the form of syringes or friable seals which are broken on activation, e.g. by twist or push.

Alternatively, the device may be in the form of a bottle. In this case, the main body of the bottle may be the dilutant reservoir which may hold dilutant in the range 0.1 liter to 2 liters. The disinfectant reservoir and the indicator reservoir (where used) may be mounted to the dilutant reservoir, e.g. on the side on the bottle, in the bottle lid or within the bottle. The disinfectant discharging means and the indicator discharging means (where used) may be arranged to wholly and completely discharge the disinfectant and indicator (where used) into the dilutant reservoir. Alternatively, the predetermined amounts of disinfectant, dilutant and/or indicator may be drawn from the respective reservoirs which hold a greater amount of the disinfectant, dilutant and/or indicator. The disinfectant discharging means and the indicator discharging means may be in the form of pumps or friable seals which are broken on activation.

The dilute disinfectant solution may be used for the following:

A solution to be applied over surgical sites before, during or after surgical procedures, e.g. via a bottle or drip-bag.

A solution to be applied to wounds via a constant stream or via a bag sealed at the edges to retain the solution over the wound. The solution is to be changed every one to three hours for freshness.

A solution to be used as a mouth rinse after oral or dental surgical procedures as well as after professional or home dental hygiene procedures.

All medical/veterinary products are subject to highly stringent clinical governance surrounding cross-infection. The proposed devices detailed above provide low cost, disposable devices which deliver the solution in a sterilized manner to the clinical site or area of use.

Various embodiments and optional features are described above. It will be appreciated that these embodiments and features can be combined in all viable permutations.

BRIEF DESCRIPTION OF DRAWINGS

The invention is diagrammatically illustrated, by way of example, in the accompanying drawings in which:—

DETAILED DESCRIPTION OF DRAWINGS

Figure 1:
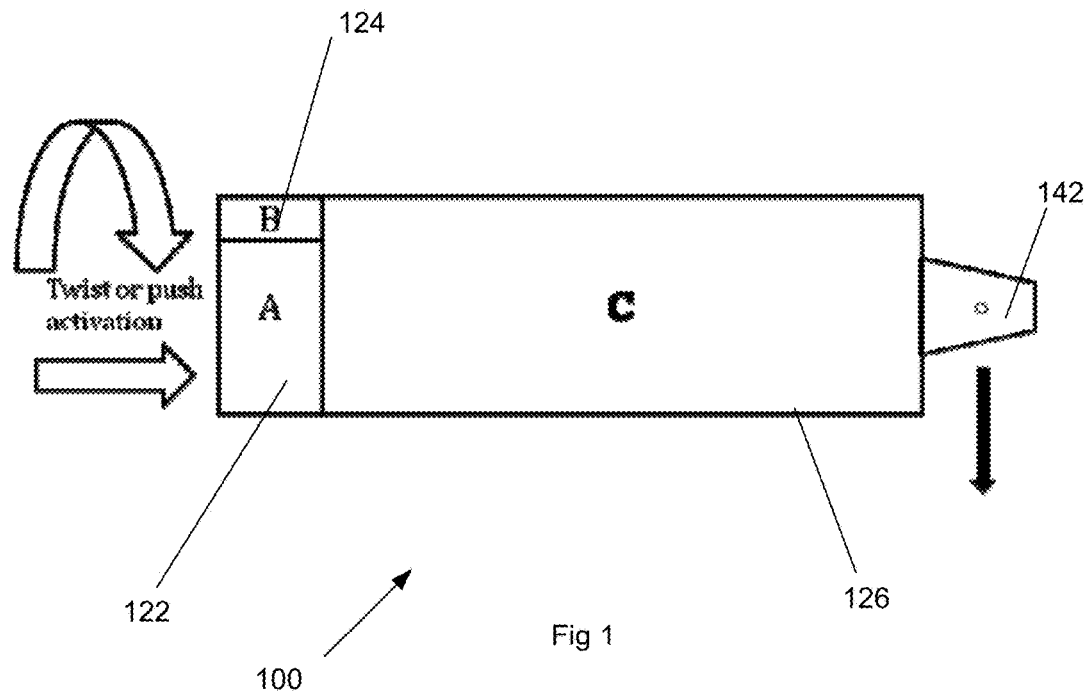
FIG. 1 is a schematic view of a first system, in the form of a spray bottle, for delivering a solution having a desired concentration.

FIG. 1 shows a first device 100 which produces a given quantity of freshly constituted "Hypo-Stream" solution for use as a surgical disinfectant and irrigation solution. The device 100 functions like a conventional pump action spray bottle delivering the correctly constituted solution as a spray via an integral nozzle at one end. As in FIG. 1, the device 100 comprises three reservoirs (122, 124, 126).

The first (or disinfectant) reservoir 122 (Chamber A) comprises 1% or 2% stabilized sodium hypochlorite solution as per the formulation of Milton 1 or Milton 2. This reservoir is opaque. The second (or indicator) reservoir 124 (Chamber B) holds an organic biocompatible and non-toxic dye. The third (or dilutant) reservoir 126 (Chamber C) comprises a chamber of sterile pure water at a pre-determined volume between 0.1 and 2 liters. The chamber has an outlet 142 in the form of a spray nozzle at the opposed end of the bottle to the first and second reservoirs. The outlet 142 may be industry standard or system specific. The outlet allows delivery of the correctly mixed dilute solution into a surgical wound or site as indicated in the direction of the arrow. As an alternative, the first and second reservoirs could be incorporated in the lid, along with the dispensing outlet (see e.g. FIG. 4).

The first and second reservoirs 122, 124 are attached to the outer wall of the third reservoir 126 to form an integral unit. The first and second reservoirs 122, 124 are situated either within the third reservoir or on the outside of the third reservoir (as shown). The first and second reservoirs 122, 124 comprise a mechanism (i.e. a disinfectant discharging means and an indicator discharging means) which is configured to allow the liquids in these reservoirs to be introduced wholly and completely into the water in the third reservoir 126. For example, there may be a seal or similar friable membrane between each of the first and second reservoirs and the third reservoir which is opened or punctured by twist or push activation by a user. In other words, activation (i.e. mixing) is a mechanically one-way process so that once mixing has occurred, the components cannot be separated. Activation is also a binary process (i.e. partial mixing is impossible).

The third reservoir thus acts as the holding chamber for mixing the three fluids together. Furthermore, since the dilutant reservoir is positioned between the outlet and the disinfectant and indicator reservoirs, the device can only discharge diluted disinfectant or dilutant. In other words, dispensing neat disinfectant is impossible because the disinfectant reservoir has no direct access to the dispensing outlet.

The relative volumes of liquid in the three reservoirs is such that the final mixed solution is the desired "Hypo-Stream" solution. This solution can be delivered by pump action to the site of surgery or to a wound.

By way of example, the third reservoir 126 may contain pure water at a pre-determined volume between 0.1 and 2 liters. The volume of solution within the second reservoir is determined so that when the solution is discharged into the third reservoir, the resultant solution has a dilution in the range of 0.025% sodium hypochlorite to 0.2% sodium hypochlorite). In other words, Milton 1 solution is diluted in the range of 1 part in 20 parts water to 1 part in 5 parts water. Thus if the third reservoir comprises 1 liter of water, there must be between 0.05 and 0.2 liters of Milton 1 solution in the first reservoir. Milton 2 solution is diluted in the range of 1 part in 40 parts water to 1 part in 10 parts water, i.e. for 1 liter of water in the third reservoir, there must be between 0.025 and 0.1 liters of Milton 2 solution. The second reservoir is thus pre-filled to ensure the resultant solution has a desired concentration within these ranges. As an example, where the disinfectant in chamber A is 2% NaOCl in 16.5% NaCl (Milton's 2 solution), the device will result in a set dilution which falls within a range of 1 in 10-1 in 40 dilution with pure water, i.e. 0.2%-0.05% NaOCl.

Thus, the device of FIG. 1 is a portable and autonomous device to produce a given quantity of freshly constituted "Hypo-Stream" solution for use as a surgical disinfectant and irrigation solution. The device is disposable and not refillable. The device consists of a bottle which may be made of a flexible transparent material. The pigment is an indicator of fresh mix as the pigment degrades over time and is a preferred feature but may be omitted to provide a wound wash bottle without any pigment. The device is designed for use for humans and animals.

Figure 2:
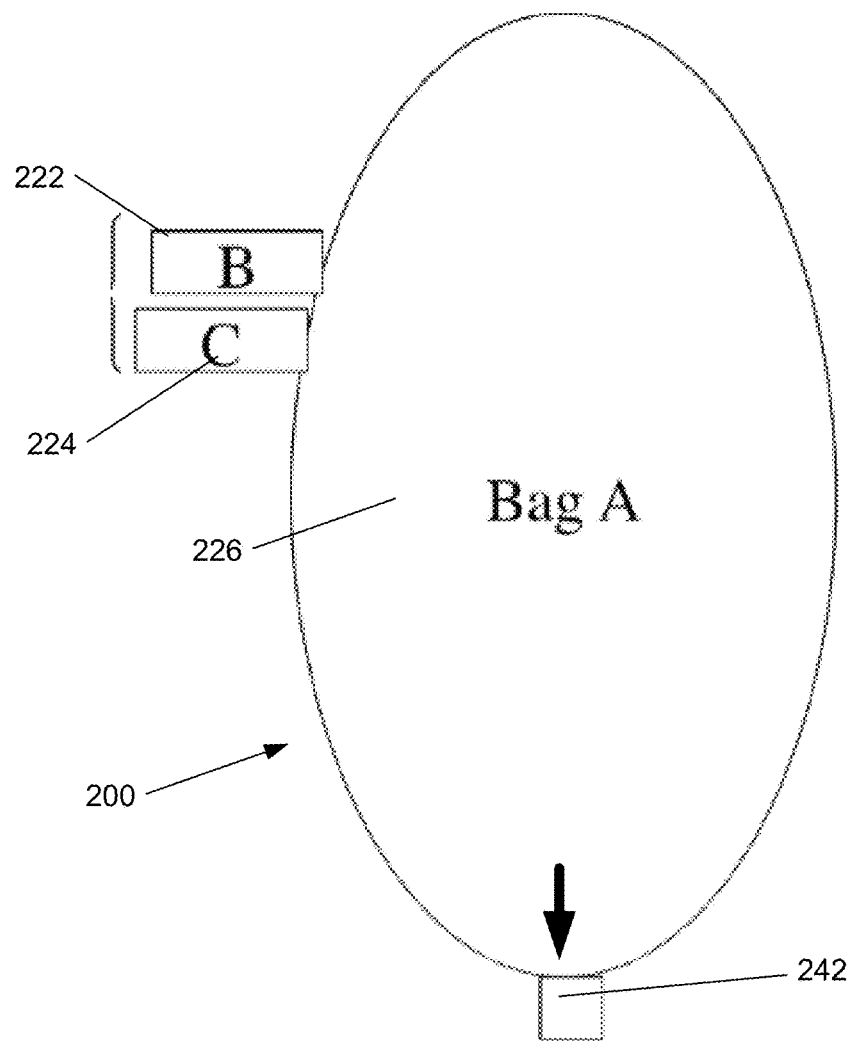
FIG. 2 is a schematic view of a second system, in the form of a drip bag, for delivering a solution having a desired concentration.

FIG. 2 shows an alternative device 200 for delivering a correctly diluted solution known as "hypo-stream" solution for use in surgical or similar situations. In this Figure, the device is disposable and not refillable.

The device 200 functions like a conventional "drip bag" and delivers gravity fed Hypo-Stream solution via conventional or system specific drip bag tubing mechanisms. As in FIG. 1, the device 200 comprises three reservoirs (222, 224, 226).

The first (or disinfectant) reservoir (Syringe B) comprises 1% or 2% stabilized sodium hypochlorite solution as per the formulation of Milton 1 or Milton 2. This reservoir is opaque. The second reservoir (Syringe C) holds an organic biocompatible and non-toxic dye. The third (or dilutant) reservoir (Bag A) comprises a large bag of pure water with an outlet 242 at the bottom allowing attachment to conventional or system specific drip bag tubing. The outlet 242 may be an industry standard connector or a connector specifically adapted to the system.

The first and second reservoirs 222, 224 are attached to the outer wall of the third reservoir 226. The first and second reservoirs 222, 224 are situated either within the third reservoir or on the outside of the third reservoir (as shown). The first and second reservoirs 222, 224 each comprise a mechanism (i.e. a disinfectant discharging means and an indicator discharging means) which is configured to allow the liquids in these reservoirs to be introduced wholly and completely into the water in the third reservoir. For example, the first and second reservoirs may be in the form of syringes which a user may discharge into the third reservoir. The third reservoir thus acts as the holding chamber for mixing the three fluids together. As with FIG. 1, the arrangement thus prevents dispensing of neat disinfectant and is a one-way, binary process.

The relative volumes of liquid in the three reservoirs is such that the final mixed solution is the desired "Hypo-Stream" solution. This solution can be delivered under force of gravity and via a drip tubing arrangement to the site of surgery or to a wound.

By way of example, the third reservoir 226 may contain pure water at a pre-determined volume between 250 ml and 2 liters. The volume of solution within the second reservoir is determined so that when the solution is discharged into the third reservoir, the resultant solution has a dilution in the ranges indicated above. In other words, Milton 1 solution is diluted in the range of 1 part in 20 parts water to 1 part in 5 parts water. Thus if the third reservoir comprises 1 liter of water, there must be between 0.05 and 0.2 liters of Milton 1 solution in the first reservoir. Milton 2 solution is diluted in the range of 1 part in 40 parts water to 1 part in 10 parts water, i.e. for 1 liter of water in the third reservoir, there must be between 0.1 and 0.025 liters of Milton 2 solution. The second reservoir is thus pre-filled to ensure the resultant solution has a desired concentration within these ranges.

Figure 3:
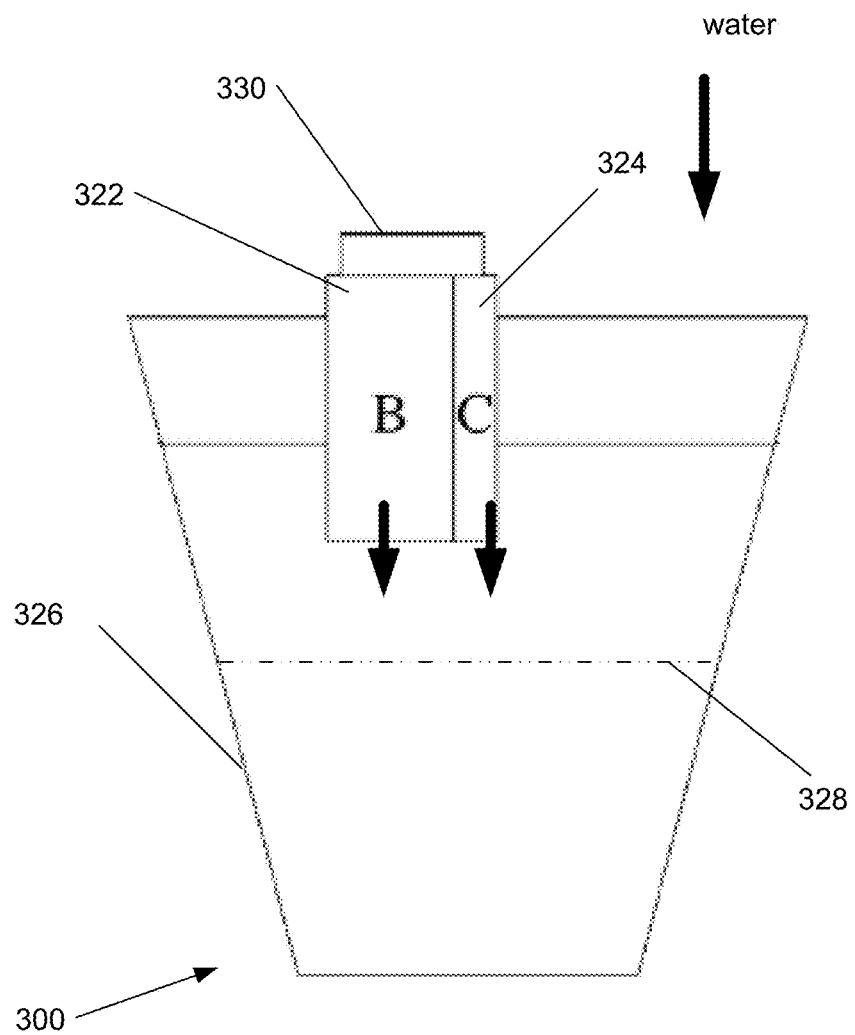
FIG. 3 is a schematic view of a third system, in the form of a mouth rinse cup, for delivering a solution having a desired concentration.

FIG. 3 shows a third device 300 which produces a given quantity of freshly constituted "Hypo-Stream" solution. This may be for use as a mouth rinse. As in FIGS. 1 and 2, the device 300 comprises three reservoirs 322, 324, 326.

The first (or disinfectant) reservoir 322 (Pump Chamber B) holds stabilized sodium hypochlorite solution. This reservoir is opaque. The second (or indicator) reservoir 324 (Pump Chamber C) contains a flavoring which is organic and biocompatible. The flavor is such that there is a noticeable degradation of the flavoring such that the solution becomes unpalatable. Since the resultant solution is most effective, if diluted immediately prior to use, the noticeable change may occur within a time frame of 45 minutes to 1 hour. In this time frame, the noticeable change occurs prior to the loss of therapeutic action of dilute disinfectant solution.

The third (or dilutant) reservoir 326 is in the form of a plastic cup (Cup A). An indication line 328 is marked on the inside (and/or outside) of the cup to indicate the appropriate level to fill with water. The first and second reservoirs 322, 324 are two side-by-side chambers mounted to the top rim of the cup. The first and second reservoirs may be considered a "piggy-back" dispenser to add buffered sodium hypochlorite solution and flavoring into the water-filled cup. When the liquids in the first and second chambers are exhausted the device may be discarded and is thus disposable. Alternatively, a new pump dispenser may be attached to the cup.

Both the first and second reservoirs 322, 324 have disinfectant and indicator discharging means which are activated by a button 330. When a user pushes the button, a single dose of the liquid from each reservoir is delivered in the direction marked by the arrows into the cup. The discharging means may be in the form of pumps or in the form of friable seals. If a pump is used, more than one dose of disinfectant and indicator may be included in the reservoirs. If a friable seal (or bag) is used, the disinfectant and indicator may be wholly and completely discharged. The cup is filled with fresh water to the line preferably before (but possibly after) activation of the dispenser. The cup thus acts as the third reservoir and the holding chamber for mixing the liquids.

The device 300 makes it possible to add the appropriate amount of 1% or 2% buffered sodium hypochlorite solution plus flavoring to a cup of fresh water. For example, the line on the cup is set such that when the first reservoir holds Milton 2 solution, a user may activate the pump once to produce a mouth rinse that is 1 part Milton (2) in 40 parts of water (with flavoring). A subsequent additional activation of the pump produces a "Hypo-Stream" solution at 1 part Milton (2) in 20 of water. The resultant "Hypo-Stream" solution is to be used as a mouth-rinse.

The device is used over the period in which it takes to exhaust the sodium hypochlorite and flavoring.

Figure 4:
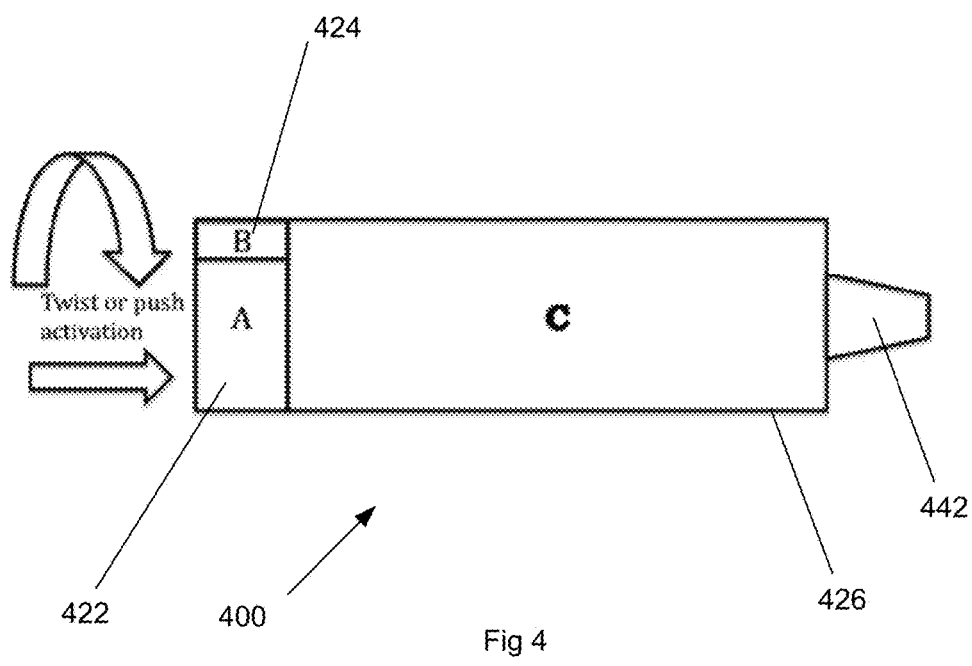
FIG. 4 is a schematic view of a fourth system, in the form of a washer bottle, for delivering a solution having a desired concentration.

FIG. 4 shows a fourth device 400 which produces a given quantity of freshly constituted "Hypo-Stream" solution for use as a surgical disinfectant and irrigation solution. The device 400 functions like a conventional washer bottle delivering gravity fed or positive pressure wound wash solution via an integral nozzle or spout at one end. As in FIG. 1, the device 400 comprises three reservoirs (422, 424, 426).

The first (or disinfectant) reservoir 422 (Chamber A) comprises 1% or 2% stabilized sodium hypochlorite solution as per the formulation of Milton 1 or Milton 2. This reservoir is opaque. The second (or indicator) reservoir 424 (Chamber B) holds an organic biocompatible and non-toxic dye. The third (or dilutant) reservoir 426 (Chamber C) comprises a chamber of sterile pure water at a pre-determined volume between 0.1 and 2 liters. The chamber has an industry standard or system specific outlet 442 in the form of a nozzle or spout at the opposed end of the bottle to the first and second reservoirs. The outlet allows delivery of the correctly mixed dilute solution into a surgical wound or site. The correctly mixed solution may be gravity fed when the bottle is held vertically or squeezed out of the bottle onto the wound of the animal or human. The solution may be poured or sprayed onto the wound.

The first and second reservoirs 422, 424 are attached to the outer wall of the third reservoir 426 to form an integral unit. The first and second reservoirs 422, 424 are situated either within the third reservoir or on the outside of the third reservoir (as shown). The first and second reservoirs 422, 424 comprise a mechanism which is configured to allow the liquids in these reservoirs to be introduced wholly and completely into the water in the third reservoir 426. For example, there may be a seal between each of the first and second reservoirs and the third reservoir which is opened or punctured by twist or push activation by a user. The third reservoir thus acts as the holding chamber for mixing the three fluids together. As with FIG. 1, the arrangement thus prevents dispensing of neat disinfectant and is a one-way, binary process.

The relative volumes of liquid in the three reservoirs is such that the final mixed solution is the desired "Hypo-Stream" solution. This solution can be delivered under force of gravity and via an industry standard drip tubing arrangement to the site of surgery or to a wound.

By way of example, the third reservoir 426 may contain pure water at a pre-determined volume between 0.1 and 2 liters. The volume of solution within the second reservoir is determined so that when the solution is discharged into the third reservoir, the resultant solution has a dilution in the range of 0.05% sodium hypochlorite to 0.2% sodium hypochlorite). In other words, Milton 1 solution is diluted in the range of 1 part in 20 parts water to 1 part in 5 parts water. Thus if the third reservoir comprises 1 liter of water, there must be between 0.05 and 0.2 liters of Milton 1 solution in the first reservoir. Milton 2 solution is diluted in the range of 1 part in 40 parts water to 1 part in 10 parts water, i.e. for 1 liter of water in the third reservoir, there must be between 0.025 and 0.1 liters of Milton 2 solution. The second reservoir is thus pre-filled to ensure the resultant solution has a desired concentration within these ranges.

Thus, the device of FIG. 4 is a portable and autonomous device to produce a given quantity of freshly constituted "Hypo-Stream" solution for use as a surgical disinfectant and irrigation solution. The device is disposable and not refillable. The device consists of a bottle made of a flexible transparent material. The pigment is an indicator of fresh mix as the pigment degrades over time and is a preferred feature but may be omitted to provide a wound wash bottle without any pigment. The device is designed for use for humans and animals.

In each of the above embodiments, the dilution is fixed for each bottle or bag design. Thus each embodiment delivers either 1 in 10 dilution or 1 in 20 dilution or 1 in 30 dilution or 1 in 40 dilution and the correct dilution can be chosen for the correct application. It is not possible for a user to alter the dilution produced by any of the designs and thus ensuring the correct dilution is delivered each time.

Each of the above embodiments has a chamber for an indicator dye. However, the use of the dye is optional and it is possible that each bottle/bag design will be manufactured without the indicator dye. The dye is such that there is either a significant color change or the solution becomes colorless within a 45 to 60 minute timeframe. The dye may be a dye such as those which are routinely used in surgical procedures with no adverse effects. Examples of suitable dyes include azafloxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red. The predetermined amount of dye is preferably low enough to prevent interaction with active components but great enough so that the dye color is visible within the dilute disinfectant solution.

The indicator dye is a preferred but optional feature and may be omitted from the embodiments described above. The following embodiments show arrangements without a reservoir for a dye but a dye reservoir could be incorporated into each of the embodiments if desired.

Figure 5A:
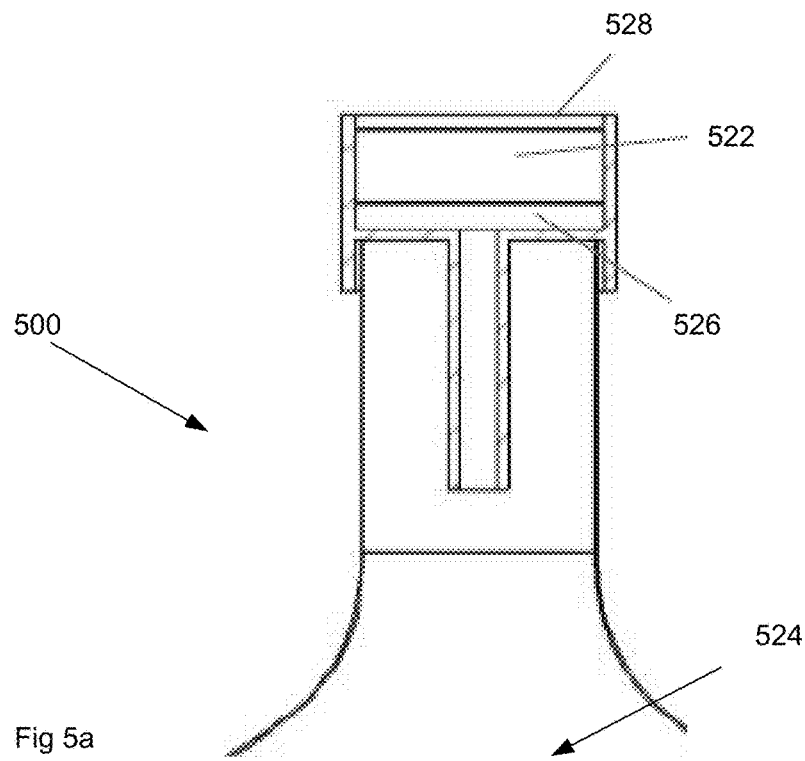
FIGS. 5a and 5b are schematic views of a fifth system, in the form of a bottle, for delivering a solution shown before and after opening, respectively.
Figure 5B:
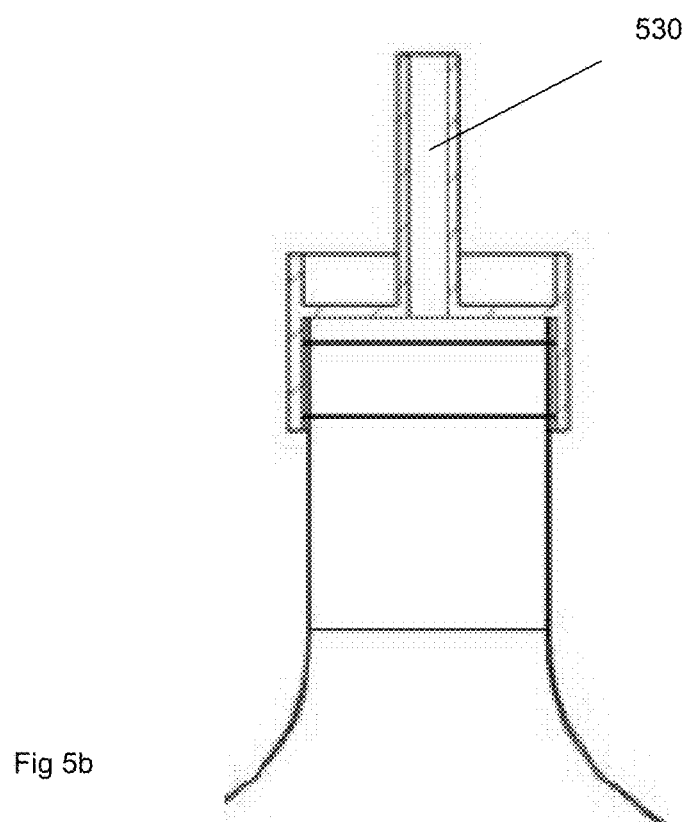

FIGS. 5a and 5b show a fifth device 500 which produces a given quantity of freshly constituted "Hypo-Stream" solution for use as a surgical disinfectant and irrigation solution. The device 500 is in the form of a bottle comprising two reservoirs (522 and 524). The first (or disinfectant) reservoir 522 comprises 1% or 2% stabilized sodium hypochlorite solution as per the formulation of Milton 1 or Milton 2 and is located in the lid of the bottle. This reservoir is opaque. The second (or dilutant) reservoir 524, namely the body of the bottle, comprises a chamber of dilutant (i.e. sterile pure water) at a pre-determined volume between 0.1 and 2 liters.

As shown in FIG. 5a, in sealed mode, the disinfectant reservoir 522 is separated from the dilutant reservoir 524 by a friable dispensing membrane 526. There is also a second friable dispensing membrane 528 on the upper surface of the lid. A third (or indicator) reservoir could optionally be included, e.g. in the lid, above or below the disinfectant reservoir, separated from the adjacent reservoirs by additional friable membranes.

As shown in FIG. 5b, in dispensing mode the lid is removed and inverted on the bottle neck. This breaks both the friable members 526, 528. In the action of screwing the inverted cap onto the bottle, the membrane 526 separating the two reservoirs is broken first to allow the disinfectant to mix with the dilutant and thus the membrane 526 forms the disinfectant discharging means. Once the membrane 526 is broken, the predetermined amount of disinfectant solution held in the disinfectant reservoir is wholly and completely discharged into the chamber (i.e. into the dilutant reservoir) which holds the predetermined amount of dilutant. These predetermined amounts are determined as set out in the embodiments above.

Thereafter, the second membrane 528 is broken to allow the diluted disinfectant to be dispensed via a spout 530. In this arrangement, mixing is a one-way, binary process. The opening of the device, i.e. removal of the lid, causes mixing and thus the arrangement is such that mixing must occur before dispensing. Moreover, the disinfectant reservoir has no direct access to the dispensing spout which reduces the chance of neat disinfectant being dispensed.

Figure 6A:
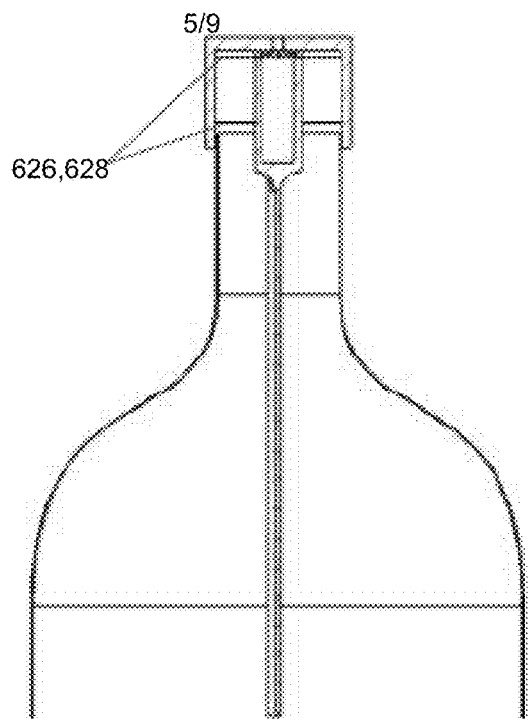
FIGS. 6a and 6b are schematic views of a sixth system, in the form of a bottle, for delivering a solution shown before and after opening, respectively.
Figure 6B:
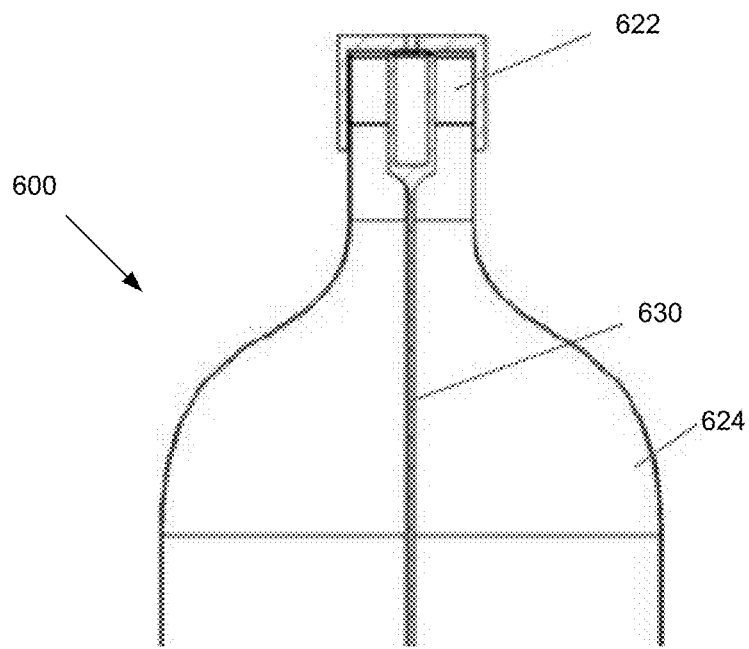

FIGS. 6a and 6b show a variant of the device 600 of FIG. 5a. The device 600 is in the form of a bottle comprising two reservoirs (622 and 624). The first (or disinfectant) reservoir 622 comprises 1% or 2% stabilized sodium hypochlorite solution as per the formulation of Milton 1 or Milton 2 and is located in the lid of the bottle. The second (or dilutant) reservoir 624, namely the body of the bottle, comprises a chamber of dilutant. The disinfectant reservoir 622 is separated from the dilutant reservoir 624 by a friable dispensing membrane 626. There is also a second friable dispensing membrane 628 on the upper surface of the lid. As with FIG. 5a, a third (or indicator) reservoir could optionally be included, e.g. in the lid, above or below the disinfectant reservoir, separated from the adjacent reservoirs by additional friable membranes.

In contrast to the embodiment of FIG. 5a, the lid is not removed but simply screwed or pushed down further to activate the device. Thus, this embodiment prevents neat dilutant and/or neat disinfectant being delivered because the lid is not removed until after mixing and there is no exposed friable membrane. The action of opening, i.e. pushing down or twisting the bottle lid down, causes the lid to move down to first break the first membrane separating the reservoirs as shown in FIG. 6b. Thus the membrane 626 forms the disinfectant discharging means. Once the membrane 626 is broken, the predetermined amount of disinfectant solution held in the disinfectant reservoir is wholly and completely discharged into the chamber (i.e. into the dilutant reservoir) which holds the predetermined amount of dilutant. These predetermined amounts are determined as set out in the embodiments above.

Further twisting to remove the lid causes the second membrane to be broken. Twisting the lid also moves paddle 630 which extends from the lid through the disinfectant reservoir and into the dilutant reservoir. The paddle 630 is an optional extra and stirs the newly mixed solution as the lid is twisted. The mixed solution may then be dispensed via the bottle's pump action dispenser (not shown) or another dispensing mechanism, e.g. squeeze bottle, pourer or even attached to a drip bag. Thus, like FIG. 5a, the arrangement is such that mixing must occur before dispensing.

In both FIGS. 5a and 6a, the lid and/or bottle may have a visual indicator making it clear that the mixing has occurred, e.g. a colored band on the bottle neck which is covered by the lid after mixing.

FIGS. 7a to 7e show a variant on the bottle device. The device 700 is in the form of a bottle comprising two reservoirs (722 and 724). The first (or disinfectant) reservoir 722 comprises 1% or 2% stabilized sodium hypochlorite solution as per the formulation of Milton 1 or Milton 2 and is located a bag within the bottle. The bag is suspended from the underside of the lid assembly. The second (or dilutant) reservoir 724, namely the body of the bottle, comprises a chamber of dilutant. The reservoirs are separated by a permanent barrier, namely the wall of the bag.

A single plunger pump 730 located in the lid 731 is arranged to draw fluid from each reservoir simultaneously. The dilutant is drawn from the second reservoir 724 into an additional dilutant reservoir 726 via a tube 728. The disinfectant is drawn from the first reservoir through an orifice 731 into an additional disinfectant reservoir (outlet) 732. Both the additional dilutant reservoir and the additional disinfectant reservoir are in the form of annuli arranged concentrically around the pump action mechanism.

The pump action mechanism comprises an upper plunger 740 mounted to a lower plunger 742 and a displacing protrusion 744. A pumping chamber 746 is formed between the lower surface of the upper plunger 740 and the upper surface of the displacing protrusion 744. The upper plunger comprises an exit passage 750 connected to a dispensing outlet 748 for dispensing dilute disinfectant.

Figures 7A, 8:
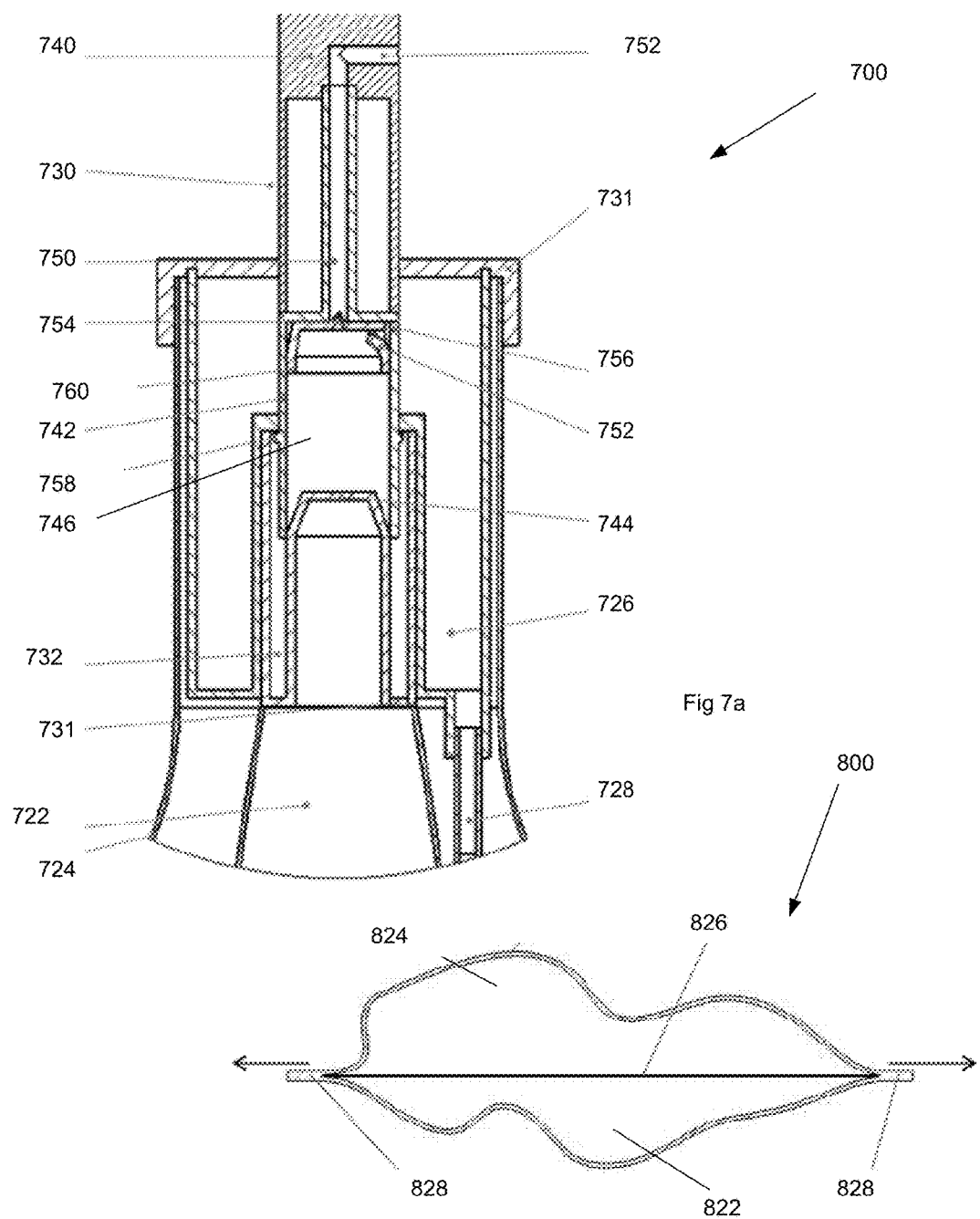
FIGS. 7a to 7e is a schematic view of a seventh system, in the form of a bottle.
FIG. 8 a schematic view of an eighth system, in the form of a bag.
Figure 7E:
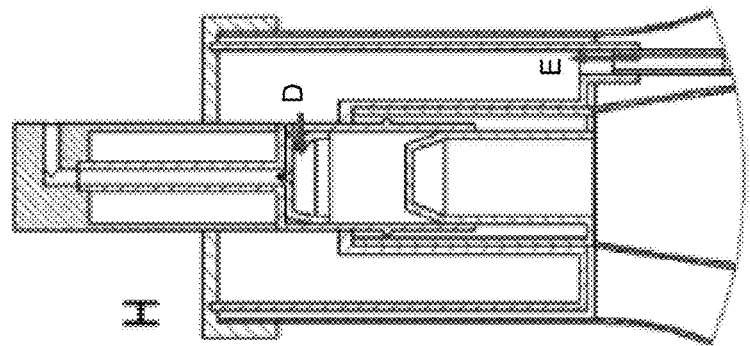
Figure 7D:
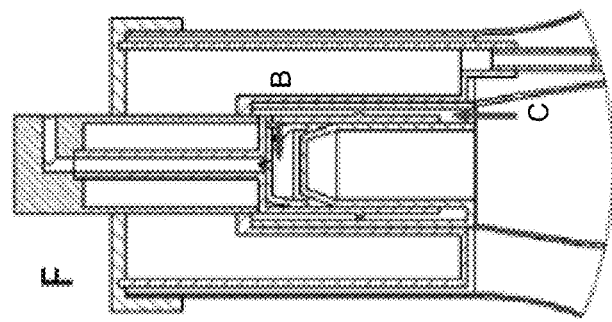
Figure 7C:
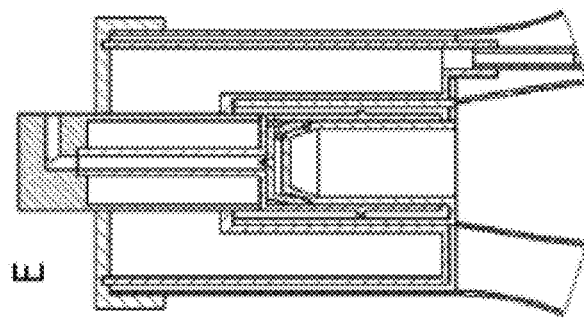
Figure 7B:
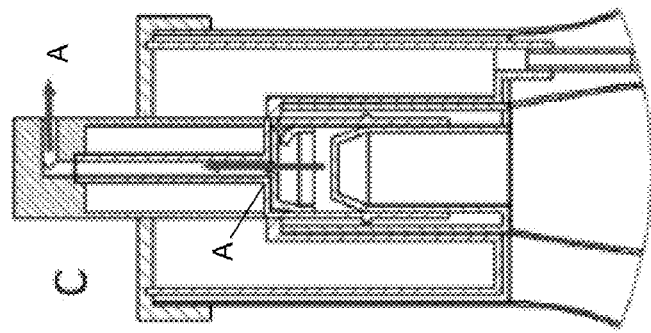

The operation of the device is shown in FIGS. 7a to 7e. The system is at rest in FIG. 7a with the pumping chamber 746 full of dilute disinfectant. As the upper plunger 740 is depressed, liquid in the pumping chamber 746 is forced out by the displacing protrusion 744. FIG. 7b shows the plunger partially depressed and shows the consequent reduction in the volume in the pumping chamber. Liquid is prevented from returning into the additional disinfectant or dilutant reservoirs by one-way discharging valve 752 and thus as shown by arrows A dilute disinfectant is forced through one-way exit valve 754 into the exit passage 750 and out from the dispensing outlet 748.

FIG. 7c shows the pumping chamber when it has been completed emptied. An elastomeric member 760 around the lower surface of the upper plunger limits the extent of the downward movement of the plunger and lessens any damage to the displacing protrusion. When force is removed from the plunger, a spring (not shown) pushes the plunger back up.

As shown in FIG. 7d, the pumping chamber now expands but the one-way exit valve 754 prevents air being drawn into the chamber. The pressure drop causes the one-way discharging valve 752 to open drawing disinfectant from the additional disinfectant reservoir 732 (arrow B) through an aperture 756 in the pumping chamber which may be termed the plunger entry orifice. Movement of the disinfectant from the additional reservoir to the pumping chamber, draws disinfectant from the disinfectant reservoir 722 into the additional disinfectant reservoir 732 (arrow C) as shown in FIG. 7d. A ring 758 around the outer wall of the pumping chamber limits the extent of the upward movement of the plunger.

The plunger continues to rise and draw in disinfectant until the aperture 756 is above the level of the additional disinfectant reservoir as shown in FIG. 7e. Accordingly, during the portion of the stroke in which the aperture is aligned with the additional disinfectant reservoir, the predetermined amount of disinfectant is drawn into the pumping chamber. Thereafter fluid is drawn from the additional dilutant reservoir 726 (arrow D) through the aperture 756 in the pumping chamber. Movement of the dilutant from the additional reservoir to the pumping chamber, draws dilutant from the dilutant reservoir 724 into the additional disinfectant reservoir 726 (arrow E). Accordingly, during the portion of the stroke in which the aperture is aligned with the additional dilutant reservoir, the predetermined amount of dilutant is drawn into the pumping chamber. Thus, the portions of the stroke during which the additional reservoirs draw from the main reservoirs determines the mixing ratio.

As an alternative, two or more pumps may be arranged to work synchronously, each one drawing fluid from each reservoir simultaneously. The drawn fluid passes into a common outlet or a set of closely spaced outlets. In this case, the ratio of the pumping volume per stroke sets the desired mixing ratio of the two fluids. The pumps are positive displacement plunger pumps.

Thus, in contrast to at least some of the other embodiments, the arrangement of FIGS. 7a to 7e may comprise enough disinfectant and dilutant to provide more than one dose of dilute disinfectant. The size of the dose is determined by the size of the pumping chamber. Once the disinfectant and dilutant are exhausted, the bottle may be discarded.

FIG. 8 shows a device 800 in the form of a bag comprising two reservoirs (822 and 824). The first (or disinfectant) reservoir 822 comprises 1% or 2% stabilized sodium hypochlorite solution as per the formulation of Milton 1 or Milton 2. The second (or dilutant) reservoir 824 comprises dilutant. The reservoirs are separated by a thin friable membrane 826 which is torn by mechanically deforming the bag. The bag is made from a thicker and more durable material than the membrane so that it is not ruptured on deforming.

The membrane 826 has a length shorter than the outer parts of the bag so that it can be broken by pulling the edges 828 of the bag in opposite directions as indicated by the arrows. Disruption of the membrane 826 causes fluid turbulence and hence mixing of the two components. Disruption of the membrane 826 also opens the dispensing aperture on the bag (not shown). As with other embodiments, the arrangement is such that mixing must occur before dispensing. The dispensing aperture is preferably located so that the disinfectant reservoir has no direct access to the dispensing aperture which reduces the chance of neat disinfectant being dispensed (e.g. located at one end of the dilutant reservoir).

A third (or indicator) reservoir could optionally be included, e.g. by including an additional friable membrane above or below the membrane shown in FIG. 8, whereby the two membranes enclose the indicator reservoir.

Figure 9:
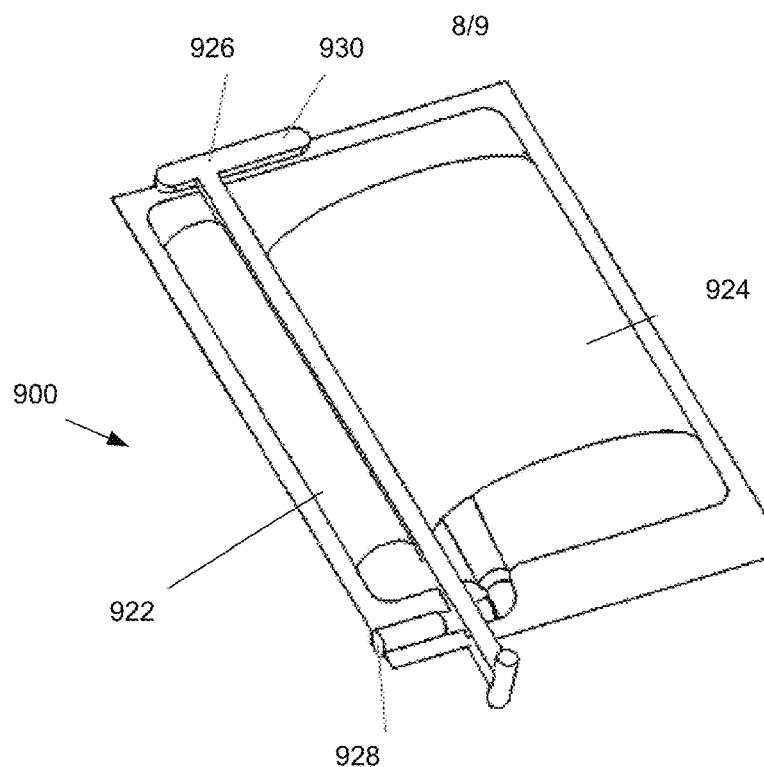
FIG. 9 is a schematic view of a ninth system, in the form of a drip bag.

FIG. 9 shows a device 900 in the form of a drip bag comprising two reservoirs (922 and 924). The first (or disinfectant) reservoir 922 comprises 1% or 2% stabilized sodium hypochlorite solution as per the formulation of Milton 1 or Milton 2. The second (or dilutant) reservoir 924 comprises dilutant. The reservoirs are separated by an external clip 926 that pinches the material of the bag along a line. The clip 926 also prevents dispensing of the contents because it pinches the tube connecting to the dispensing outlet 928.

Removal of the clip causes the two reservoirs to form a single mixing chamber and then to open the passage to the dispensing outlet. The clip is adapted, e.g. has a T-piece 930, to cause turbulence and promote fluid mixing. The clip may also only be slid off in one direction, i.e. over the outlet 928. In this way, no fluid escapes the device until mixing has occurred. Furthermore, the clip also preferably slides off over the disinfectant reservoir thus ensuring that the disinfectant can only be discharged via the mixing chamber, i.e. not neat. The outlet of the device is also disposed close to line dividing the two reservoirs so that the dispensed fluid is approximately of the correct concentration even if mixing is incomplete.

A third (or indicator) reservoir could optionally be included, e.g. by dividing the disinfectant reservoir into two chambers, one holding disinfectant and one holding indicator. As the clip slides over the two chambers, the contents are discharged into the dilutant reservoir.

Figure 10A:
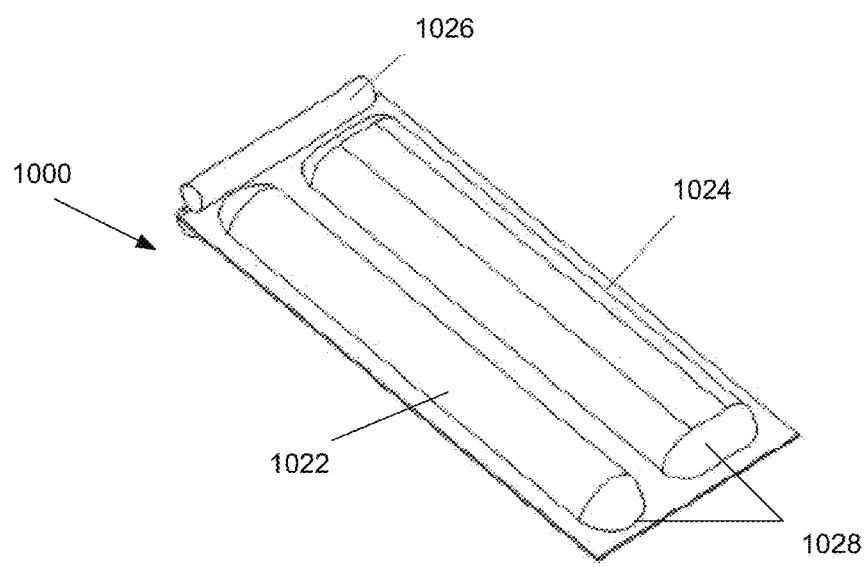
FIGS. 10a and 10b are schematic views of two further systems, in the form of a syringes.

FIG. 10a shows a device 1000 in the form of a dual plunger comprising two reservoirs (1022 and 1024). The first (or disinfectant) reservoir 1022 comprises 1% or 2% stabilized sodium hypochlorite solution as per the formulation of Milton 1 or Milton 2. The second (or dilutant) reservoir 1024 comprises dilutant. The relative cross-sectional areas of the two reservoirs determines the mixing ratio. A roller 1026 is positioned at one end of the device and at the opposed end of the device both reservoirs have friable membranes 1028.

The roller and the friable membranes cooperate to form the dilutant discharging means and the disinfectant discharging means. The dilutant and disinfectant are dispensed simultaneously by moving roller 1026 across the reservoirs which forces the liquids through the friable membranes 1028. In this arrangement, there is no mixing before dispensing. Nevertheless, dispensing is a one-way, binary process. The arrangement ensures that the liquids are dispensed simultaneously and will thus be in the correct concentration because of the relative cross-sectional areas of the two reservoirs.

Figure 10B:
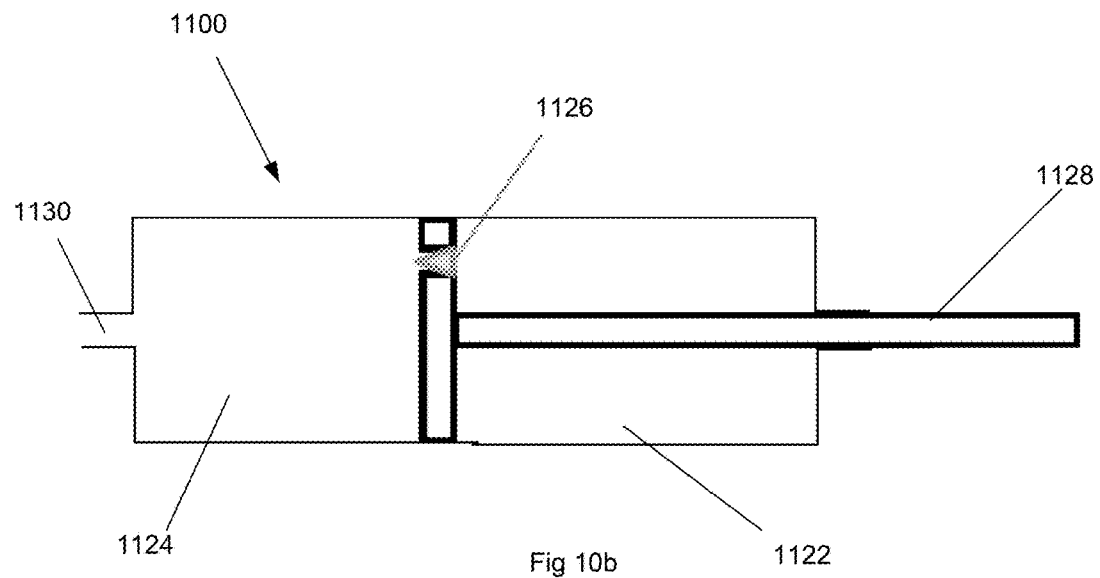

FIG. 10b shows a device 1100 in the form of a syringe comprising two reservoirs (1122 and 1124). The first (or disinfectant) reservoir 1122 comprises 1% or 2% stabilized sodium hypochlorite solution as per the formulation of Milton 1 or Milton 2. The second (or dilutant) reservoir 1124 comprises dilutant. The relative volumes of the two reservoirs determines the mixing ratio. The two reservoirs are separated by the head 1128 of the syringe plunger.

The head comprises either a one-way valve or a friable membrane 1126. Movement of the head away from the dispensing port 1130 causes the valve or membrane to open and mixing to occur. After mixing, the head is moved in the opposite direction to dispense the dilute disinfectant. There is a ratchet (not shown) to prevent movement of the head towards the outlet before mixing has occurred. Dispensing is a one-way, binary process, with mixing before dispensing and the only access for the disinfectant to the outlet is via the dilutant reservoir.

Figure 11:
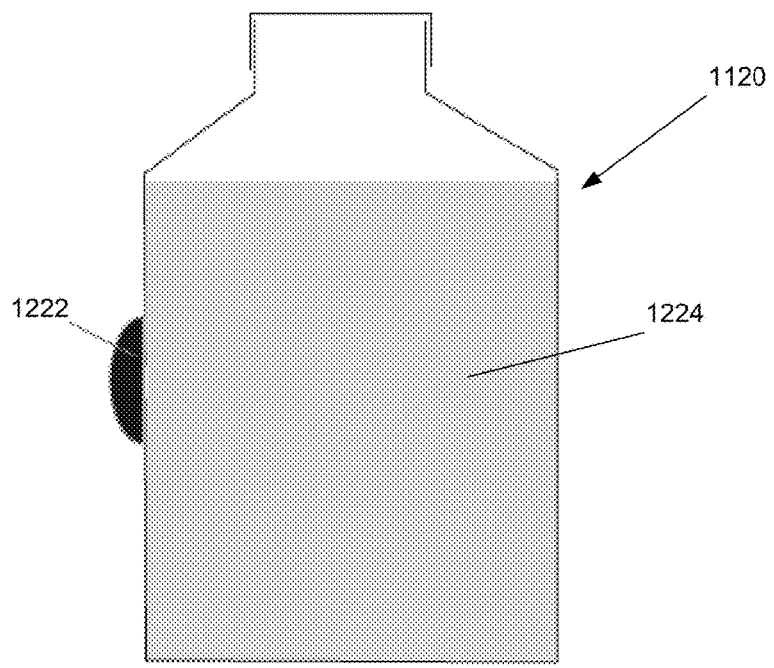
FIG. 11 is a schematic view of another system, in the form of a bottle.

FIG. 11 shows a device 1120 in the form of a bottle comprising two reservoirs (1222 and 1224). The first (or disinfectant) reservoir 1222 comprises 1% or 2% stabilized sodium hypochlorite solution as per the formulation of Milton 1 or Milton 2 and is in the form of a blister pack on the side of the bottle. The second (or dilutant) reservoir 1224 comprises dilutant and is the body of the bottle. The relative volumes of the two reservoirs determines the mixing ratio. Dispensing is a one-way, binary process with mixing before dispensing and the only access for the disinfectant to the outlet is via the dilutant reservoir.

The two reservoirs are separated by a friable inner membrane positioned over a hole in the bottle wall. The inner membrane is broken by pressing on the blister. A dye may be used to color the disinfectant in the blister so that it is obvious when mixing has occurred. Alternatively, a second blister pack could be mounted on the bottle to form a third (disinfectant reservoir).

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of treating infection, preventing infection or aiding healing in a mammal comprising administering to said mammal an effective amount of a composition comprising dilute stabilized sodium hypochlorite solution and a dye to show that the dilute stabilized sodium hypochlorite solution is fresh and active by means of a color change within a period of one hour after said dilute stabilized sodium hypochlorite solution is prepared, wherein said dye selected from the group consisting of azafloxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red.

2. The method according to claim 1, wherein the sodium hypochlorite is in a concentration range of 0.025%-0.2%.

3. The method according to claim 1, wherein the sodium hypochlorite is in a concentration range of 0.05%-0.1%.

4. The method according to claim 1, wherein the dilute stabilized sodium hypochlorite solution further comprises sodium chloride.

5. The method according to claim 1, wherein the dilute stabilized sodium hypochlorite solution further comprises sodium chloride in a concentration range of 0.41%-1.65%.

6. The method according to claim 1, wherein said dye also shows that the disinfectant is at the correct dilution.

7. The method according to claim 1, wherein said dye also shows the strength of disinfectant in said solution.

8. The method according to claim 1, wherein said dye is degraded by the chemical action of the disinfectant.

9. The method according to claim 1, wherein said dye is selected so that it degrades and shows a change in property over the same period in which the activity of the selected dilution of said stabilized sodium hypochlorite solution degrades.

10. The method according to claim 1, wherein said dilute stabilized sodium hypochlorite solution is buffered to a pH of from 5-10.

11. The method according to claim 1, wherein said dilute stabilized sodium hypochlorite solution is buffered to a pH of from 5-10 and the buffer is selected from the group consisting of a phosphate/phosphoric acid buffer, a borate/boric acid buffer, and a citrate/citric acid buffer.

12. The method according to claim 1, wherein said dilute stabilized sodium hypochlorite solution is buffered to a pH of from 6-8.

13. A method of assessing the disinfecting activity of dilute stabilized sodium hypochlorite solution, the method comprising mixing said solution with a dye to show that the dilute stabilized sodium hypochlorite solution is fresh and active by means of a color change within a period of one hour after said dilute stabilized sodium hypochlorite solution is prepared, wherein said dye is selected from the group consisting of azafloxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red.

14. The method according to claim 13, wherein the sodium hypochlorite is in a concentration range of 0.025%-0.2%.

15. The method according to claim 13, wherein the sodium hypochlorite is in a concentration range of 0.05%-0.1%.

16. The method according to claim 13, wherein the dilute stabilized sodium hypochlorite solution further comprises sodium chloride.

17. The method according to claim 13, wherein the dilute stabilized sodium hypochlorite solution further comprises sodium chloride in a concentration range of 0.41%-1.65%.

18. The method according to claim 13, wherein said dye also shows that the disinfectant is at the correct dilution.

19. The method according to claim 13, wherein said dye also shows the strength of disinfectant in said solution.

20. The method according to claim 13, wherein said dye is degraded by the chemical action of the disinfectant.

21. The method according to claim 13, wherein said dye is selected so that it degrades and shows a change in property over the same period in which the activity of the selected dilution of said stabilized sodium hypochlorite solution degrades.

22. The method according to claim 13, wherein said dilute stabilized sodium hypochlorite solution is buffered to a pH of from 5-10.

23. The method according to claim 13, wherein said dilute stabilized sodium hypochlorite solution is buffered to a pH of from 5-10 and the buffer is selected from the group consisting of a phosphate/phosphoric acid buffer, a borate/boric acid buffer, and a citrate/citric acid buffer.

24. The method according to claim 13, wherein said dilute stabilized sodium hypochlorite solution is buffered to a pH of from 6-8.

25. A method of irrigating surgical sites or wounds in a mammal comprising administering to said mammal an effective amount of a composition comprising dilute stabilized sodium hypochlorite solution and a dye to show that the dilute stabilized sodium hypochlorite solution is fresh and active by means of a color change within a period of one hour after said dilute stabilized sodium hypochlorite solution is prepared, wherein said dye is selected from the group consisting of azafloxin, basic blue (nil blue sulphate), bismarck brown, basic red (rhodamine 6G), bengal red, brilliant crysyl blue, eosin, fluorescein, gentian violet, indocyanine green, janus green, methylene green, methylene blue, neutral red, trypan blue, and trypan red.

26. The method according to claim 25, wherein the sodium hypochlorite is in a concentration range of 0.025%-0.2%.

27. The method according to claim 25, wherein the sodium hypochlorite is in a concentration range of 0.05%-0.1%.

28. The method according to claim 25, wherein the dilute stabilized sodium hypochlorite solution further comprises sodium chloride.

29. The method according to claim 25, wherein the dilute stabilized sodium hypochlorite solution further comprises sodium chloride in a concentration range of 0.41%-1.65%.

30. The method according to claim 25, wherein said dye also shows that the disinfectant is at the correct dilution.

31. The method according to claim 25, wherein said dye also shows the strength of disinfectant in said solution.

32. The method according to claim 25, wherein said dye is degraded by the chemical action of the disinfectant.

33. The method according to claim 25, wherein said dye is selected so that it degrades and shows a change in property over the same period in which the activity of the selected dilution of said stabilized sodium hypochlorite solution degrades.

34. The method according to claim 25, wherein said dilute stabilized sodium hypochlorite solution is buffered to a pH of from 5-10.

35. The method according to claim 25, wherein said dilute stabilized sodium hypochlorite solution is buffered to a pH of from 5-10 and the buffer is selected from the group consisting of a phosphate/phosphoric acid buffer, a borate/boric acid buffer, and a citrate/citric acid buffer.

36. The method according to claim 25, wherein said dilute stabilized sodium hypochlorite solution is buffered to a pH of from 6-8.

* * * * *